United States Patent
Bergmann et al.

(10) Patent No.: US 8,252,548 B2
(45) Date of Patent: Aug. 28, 2012

(54) IN VITRO METHOD FOR THE DETECTION OF EARLY-STAGE LIVER DAMAGE

(75) Inventors: Andreas Bergmann, Berlin (DE); Joachim Struck, Berlin (DE); Nils G. Morgenthaler, Berlin (DE)

(73) Assignee: B.R.A.H.M.S GmbH, Hennigsdorf (DE)

( * ) Notice: Subject to any disclaimer, the term of this patent is extended or adjusted under 35 U.S.C. 154(b) by 417 days.

(21) Appl. No.: 12/299,829

(22) PCT Filed: May 8, 2007

(86) PCT No.: PCT/EP2007/004063
§ 371 (c)(1),
(2), (4) Date: Jan. 8, 2009

(87) PCT Pub. No.: WO2007/128570
PCT Pub. Date: Nov. 15, 2007

(65) Prior Publication Data
US 2009/0176267 A1    Jul. 9, 2009

(30) Foreign Application Priority Data

May 8, 2006   (DE) .......................... 10 2006 021 406

(51) Int. Cl.
*C12Q 1/34* (2006.01)
(52) U.S. Cl. ........................................ 435/18; 435/7.94
(58) Field of Classification Search .................... 435/18, 435/7.94
See application file for complete search history.

(56) References Cited

U.S. PATENT DOCUMENTS

| | | | |
|---|---|---|---|
| 7,413,850 B2 | 8/2008 | Bergmann et al. | |
| 7,645,584 B2 | 1/2010 | Svetlov et al. | |
| 2004/0235953 A1* | 11/2004 | Summar et al. | 514/565 |
| 2006/0115869 A1* | 6/2006 | Bergmann et al. | 435/15 |
| 2007/0238864 A1* | 10/2007 | Ottens et al. | 530/413 |
| 2010/0196942 A1 | 8/2010 | Svetlov et al. | |

FOREIGN PATENT DOCUMENTS

| | | |
|---|---|---|
| WO | 00/73322 | 12/2000 |
| WO | 03/089933 A1 | 10/2003 |

OTHER PUBLICATIONS

Ozaki M. et al. Enzyme Linked Immunosorbent Assay of Carbamoylphosphate Synthetase 1. Enzyme Protein vol. 95, pp. 213-221, 1994.*
Elgudin L. et al. Ammonia Induced Encephalopathy From Valproic Acid in a Bipolar Patient: Case Report. International J Psychiatry in Medicine 33(1)91-96, 2003.*
Preliminary Report on Patentability including Written Opinion of the ISA for priority International Application No. PCT/EP2007/004063.
Rolf Teschke, "Toxische Leberschäden durch Arzneimittel", Deutsches Ärzteblatt, Journal 98(40), Oct. 5, 2001, 2584-2589. (Abstract Only).
Tabuchi et al., "Regulation of Genes for Inducible Nitric Oxide Synthase and Urea Cycle Enzymes in Rat Liver in Endotoxin Shock", Biochemical and Biophysical Research Communications 268, vol. 268(1), 2000, 221-224.
Haraguchi et al., "Cloning and sequence of a cDNA encoding human carbamyl phosphate synthetase I: molecular analysis of hyperammonemia", GENE, 107 (1991) 335-340.
Holden et al., "Carbamoyl phosphate synthetase: an amazing biochemical odyssey from substrate to product", CMLS, Cellular and Molecular Life Sciences, vol. 56 (1999) 507-522.
Ozaki et al., "Enzyme-Linked Immunosorbent Assay of Carbamoylphosphate Synthetase I: Plasma Enzyme in Rat Experimental Hepatitis and Its Clearance", Enzyme Protein 1994-95; vol. 48, 213-221.
Yin, et al., "Participation of different cell types in the restitutive response of the rat liver to periportal injury induced by allyl alcohol", Journal of Hepatology 1999; vol. 31; 497-507.
Tong-hua et al., "Carbamyl Phosphate Synthetase I" Chinese Medical Journal, 102(8): 630-638, 1989.
Struck et al., "Release of the Mitochondrial Enzyme Carbamoyl Phosphate Synthase Under Septic Conditions", Shock, vol. 23(6), 533-538, 2005.
Navarro et al., "Drug-Related Hepatotoxicity", The New England Journal of Medicine, vol. 354(7), Feb. 16, 2006, 731-739.

* cited by examiner

*Primary Examiner* — Ralph Gitomer
(74) *Attorney, Agent, or Firm* — Heslin Rothenberg Farley & Mesiti P.C.

(57) ABSTRACT

Disclosed is an in vitro method for the identification and the concomitant monitoring of the therapy and cure of drug-induced or addictive substance-induced liver damage, in which the occurrence of the human enzyme carbamoyl synthase 1 (CPS 1) or its concentration is determined in serum or plasma samples from patients who are being or have been treated with potentially liver-damaging drugs, or from people who take harmful stimulants and addictive substances or are exposed to hepatotoxic substances.

7 Claims, 1 Drawing Sheet

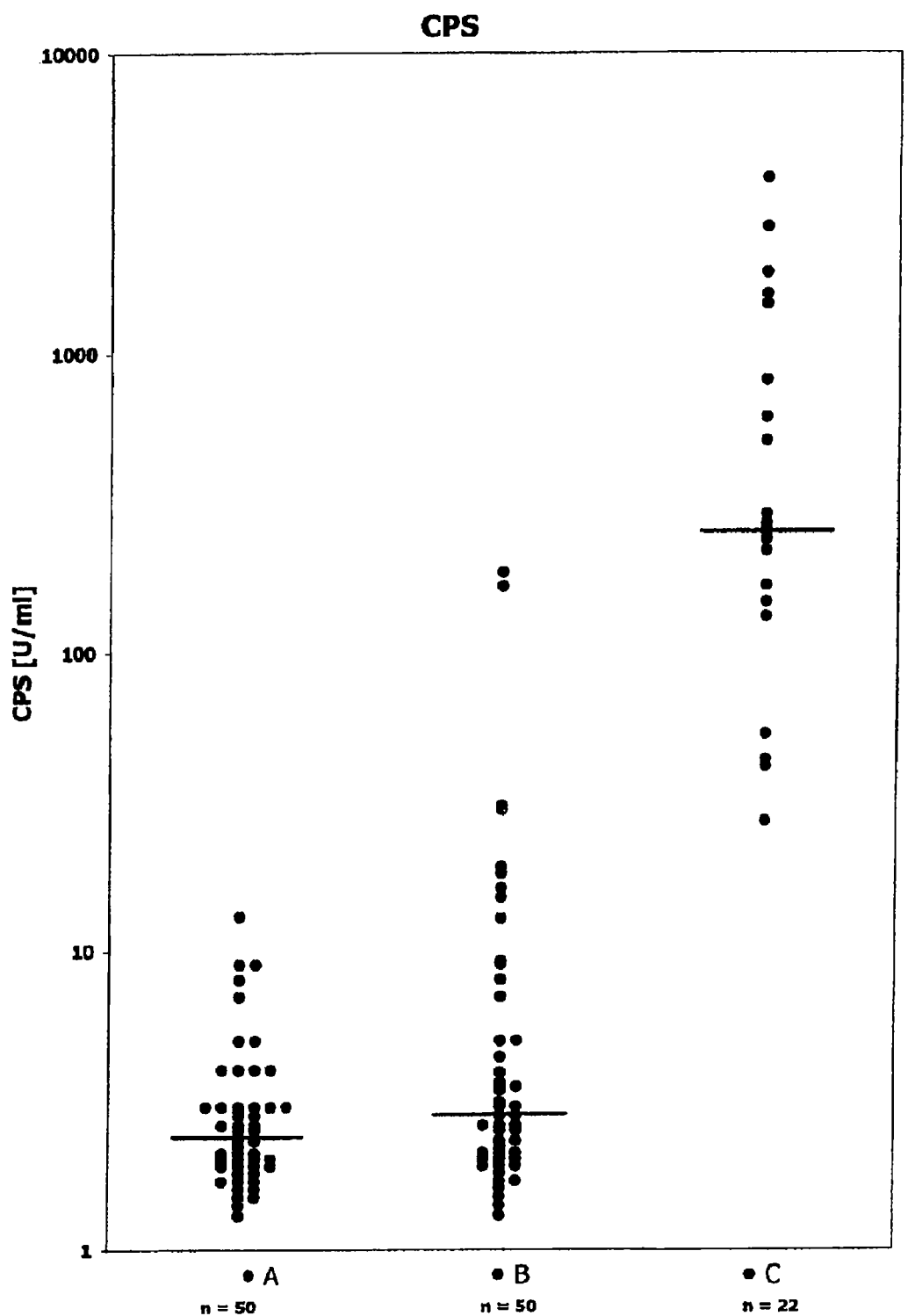

SEQUENCE LISTING

<160> NUMBER OF SEQ ID NOS: 2

<210> SEQ ID NO 1
<211> LENGTH: 17
<212> TYPE: PRT
<213> ORGANISM: Artificial
<220> FEATURE:
<223> OTHER INFORMATION: Synthetic

<400> SEQUENCE: 1

Cys Glu Phe Glu Gly Gln Pro Val Asp Phe Val Asp Pro Asn Lys Gln
1               5                   10                  15

Asn

```
<210> SEQ ID NO 2
<211> LENGTH: 15
<212> TYPE: PRT
<213> ORGANISM: Artificial
<220> FEATURE:
<223> OTHER INFORMATION: Synthetic

<400> SEQUENCE: 2

Cys Phe His Gly Thr Ser Ser Arg Ile Gly Ser Ser Met Lys Ser
1               5                   10                  15
```

IN VITRO METHOD FOR THE DETECTION OF EARLY-STAGE LIVER DAMAGE

CROSS REFERENCE TO RELATED APPLICATIONS

This application is a 371 filing of PCT International application no. PCT/EP2007/004063 filed May 8, 2007 and published in German as WO 2007/128570 on Nov. 15, 2007, which claims the priority of German application no. 102006021406.4 filed May 8, 2006. The disclosures of these applications and all other patents, published applications and other references cited herein are hereby incorporated by reference in their entirety.

The invention relates to a novel in vitro method for the identification and early identification and for the concomitant monitoring of the therapy and cure of, in particular, drug- and addictive substance-induced liver damage by determining a biomarker not yet used or proposed for these purposes in the circulation of a human patient, this novel biomarker being detectable at an earlier stage than other liver biomarkers currently introduced into routine medicine for the diagnosis of liver damage.

It is known that numerous drugs useful per se and widely prescribed can lead to liver damage in individual persons of this disposition or under certain unfavorable conditions (for example additional loading of the organism by further drugs, alcohol consumption, other external loads and nutritional state and habits).

Such drugs also designated as "potentially liver-damaging drugs" in the present application are to be found in a very wide range of active substance classes with applications for virtually all clinical indications, it being known that the risk is particularly high in the case of some drugs.

The liver damage caused by the drugs manifests itself clinically in a variety of symptoms which as such are not particular informative. For example, loss of appetite, exhaustion, giddiness, weight loss, nausea, vomiting, fever, pain in the upper right abdominal region, arthralgias, myalgias, itching, rashes and discoloration of excretions may be mentioned. The most striking symptom, which however occurs only in a relatively far advanced state, is yellowing of the eyes and even of the skin, which must then be a reason for an immediate gastroenterological diagnosis since severe and possibly irreversible damage to the liver is to be feared. A discussion of the problems is to be found, for example, in R. Teschke, Dt. Ärzteblatt 2001, 98: A2584-2589; or in Victor J. Navarro, M. D., and John R. Senior, Drug-Related Hepatotoxicity, N Engl J Med 2006; 354: 731-739.

Since possible liver damage due to the side effects of drugs should be detected as early as possible in the interest of the patient, of public health and of avoidance of subsequent negative costs to the economy, but the diagnostic means available to date are not suitable or suitable only to an insufficient extent for such an early identification, there is a considerable need for novel reliable and readily determinable diagnostic parameters for the early identification of liver damage which is attributable to the external supply of liver-damaging substances, such as, in particular, of drugs, but also of harmful stimulants and addictive substances (narcotics, stimulants, alcohol) or other substances to which the persons and groups of persons are exposed.

Since blood tests are part of routine medicine, a novel reliable biomarker which can be easily and safely determined in a blood sample and meets the above-mentioned requirements would be very highly desirable.

The present invention relates to the identification of a novel biomarker of this type and is used for the identification and early identification of liver damage, in particular due to the use of drugs or addictive substances.

The claims are intended to protect under patent law in vitro diagnostic methods in which the humoral biomarker carbamoyl phosphate synthetase (CPS 1) or its fragments appearing in the blood even at an early stage in particular of drug-related or addictive substance-related liver damage or measureable in elevated concentrations is used for the identification of liver damage which is caused by the use of drugs (pharmaceuticals, medicaments) or addictive substances (narcotic, alcohol) or by other liver-damaging substances or infectious agents/particles. The novel biomarker CPS 1 is detectable at an earlier stage than other liver biomarkers currently introduced in routine medicine for the diagnosis of liver damage. Its detection therefore has the considerable advantage that liver damage is detectable at such an early stage that immediate intervention can, with high prospects for success, prevent permanent late damage owing to damage which has become chronic.

The terms "drug" and "addictive substance" are used in the present application in an encompassing, wide sense for physiologically active substances which a person takes or receives and which may cause damage to the liver under certain conditions and/or in certain correspondingly disposed persons. Thus, without the following exemplary list being intended to be exhaustive, the term "drug" comprises in particular all prescription or over-the-counter (OTC) substances and preparations of substances in the meaning of the drugs law, which, by use on or in the human body, are intended to cure, to alleviate, to prevent or to identify diseases, affections, physical injuries or pathological complaints. The drugs may be active substances and active substance preparations synthesized and/or processed to give drugs by the pharmaceutical industry, but they may also be substances and preparations of substances which are used in naturopathy, e.g. phytopharmaceuticals or so-called functional food supplements.

Furthermore, the area of the present invention is not intended to be limited to "drugs" in the above broadly defined sense but also to include the effects of other pharmacologically active substances which are taken by humans for purposes other than curative purposes, such other substances being summarized herein by the term "addictive substances" and including, for example, narcotics and potentially health-damaging stimulants.

From an even more fundamental point of view, the method according to the invention relates to a special case—but one which is particularly important for medical practice and public health—of the early identification of liver damage which is caused by virtually any liver-damaging (hepatotoxic) substances but also by liver-damaging viruses, microorganisms and parasites. Thus, the area of the invention can also be extended to cover the health-damaging effects of pharmacologically active substances or infectious agents which the persons do not consciously take but which they take up, for example, as impurities of foods or as toxic environmental chemicals or as a result of other permanent environmental influences in their respective living space.

The method is also suitable, for example, for the early identification of liver damage which is triggered by the action of possibly unknown substances to which patients, individuals or certain population or professional groups are exposed. Thus, the method can serve, for example, for detecting hepatotoxic substances in population groups with certain lifestyles or in certain professional groups if statistically significant elevations of the CPS 1 concentrations in the blood can be detected in such a population group.

By way of example and without being intended to limit the scope of protection of the invention thereby, nonsteroidal anti inflammatory drugs (NSAIDs), other analgesics, anabolic steroids, hormonal contraceptives, antigout agents, statins, inhalational anesthetics, antibiotics, sulfonamides, tuberculostatic agents, antitumor agents, psychotropic drugs, cardiovascular agents, in particular antihypertensive agents, phytopharmaceutical agents may be mentioned as drug groups to which the potentially liver-damaging drugs can be assigned.

Paracetamol, tetracyclines, ibuprofen, chlorpromazine, captopril, enalapril, halothane, kava kava, streptomycin, isoniazide and/or rifampicin may be mentioned by way of example as more specific drugs or drug groups of this type.

The diagnosis of established liver damage which is caused by infectious particles of microbial or viral origin, which are not to be designated as "drugs" or "addictive substances", is not within the actual scope of the present invention. In this area, however, the present invention may have the advantage that identification of such liver damage too is possible as early identification, so that intervention can be made at an earlier time than is usual today. In the case of liver-damaging substances, the intervention is a search for the actual harmful substances and the termination of exposure. If an infection is found to be the trigger, suitable therapeutic countermeasures, for example with the administration of suitable agents, for example antiviral agents or optionally interleukins, can be begun earlier than is usual today.

The present invention is based on the surprising finding that, in the case of drug-related and in particular the associated addictive substance-related liver damage, clearly increased concentrations of the enzyme carbamoyl phosphate synth(et)ase (CPS 1) or a strong CPS 1 immunoreactivity are detectable even at an early stage in which liver damage is otherwise not yet clinically manifest, in particular in clear contrast to persons who are treated with the same drugs but in whom no liver damage develops—for example because they as individuals are less sensitive or are not exposed to certain further additional risk factors.

This finding makes CPS 1 a humoral biomarker which is suitable in particular for the early identification of drug-related and other liver damage.

Using an immunoassay which had been developed by the applicant in relation to sepsis diagnosis and which selectively permits the detection and the concentration measurement of CPS 1 in a serum or plasma of a human patient, it was shown on the applicant's premises that drug-related liver damage can be identified at a particularly early stage by a CPS 1 determination, in particular before clinical symptoms of liver damage occur and before other known markers (liver enzymes) which are introduced as clinical markers for liver diseases are found at significantly increased levels, and before the liver damage possibly becomes irreversible.

CPS 1 and CPS 1 fragments having CPS 1 immunoreactivity have not yet played a practical role to date for medical diagnosis.

The enzyme CPS 1 (E. C. 6.3.4.16) itself has, however, long been well known. It catalyzes the conversion of ammonia, bicarbonate and 2-ATP with formation of carbamoyl phosphate in the first step of the urea cycle. It also plays a role in the biosynthesis of arginine, which in turn is a substrate for the biosynthesis of NO, for example in the case of an endotoxin shock (cf. Shoko Tabuchi et al., Regulation of Genes for Inducible Nitric Oxide Synthase and Urea Cycle Enzymes in Rat Liver in Endotoxin Shock, Biochemical and Biophysical Research Communications 268, 221-224 (2000)). CPS 1 should be distinguished from the cytosolic enzyme CPS 2 (E. C. 6.3.5.5.) which likewise plays a role in the urea cycle but processes the substrate glutamine. It is known that CPS 1 is localized in mitochondria and occurs in lived tissue in this form in large amounts (it accounts for 2-6% of total liver protein). Its amino acid sequence and genetic localization have long been known (cf. Haraguchi Y. et al., Cloning and sequence of a cDNA encoding human carbamoyl phosphate synthetase I: molecular analysis of hyperammonemia, Gene 1991, Nov. 1; 107(2): 335-340; cf. also the publication WO 03/089933 A1 of the applicant). Regarding its physiological role, reference may be made to review articles such as, for example, H. M. Holder et al., carbamoyl phosphate synthetase: an amazing biochemical odyssey from substrate to product, CMLS Cell. Mol. Life Sci. 56 (1999) 507-522, and the literature referred to therein, and the introduction of the publication by Mikiko Ozaki et al., Enzyme-Linked Immunosorbent Assay of Carbamoylphosphate Synthetase I: Plasma Enzyme in Rat Experimental Hepatitis and Its Clearance, Enzyme Protein 1994, 95:48:213-221.

According to Li Yin et al., Participation of different cell types in the restitutive response of the rat liver to periportal injury induced by allyl alcohol, Journal of Hepatology 1999, 31:497-507, an increase of the CPS 1 expression can be observed in all hepatocytes in histological investigations after three days in the case of liver damage by allyl alcohol.

It was furthermore found that greatly increased immunological CPS 1 activity (detected with an ELISA with anti-rat CPS 1 IgG from rabbits) is present in rat plasma in the rat model in the case of acute hepatitis experimentally induced by administration of galactosamine, in particular 24-48 h after the treatment with the hepatitis-inducing galactosamine. During acute hepatitis, CPS 1 fragments having molar masses of about 140 and 125 kDa were also increasingly identifiable in rat plasma, without other more detailed characterization (sequence assignment), whereas no CPS 1 fragments having CPS 1 immunoreactivity were observable in human autopsy samples in an accompanying immunoblotting analysis (Mikiko Ozaki et al., loc. cit.).

In a paper by Liu Tong-Hua et al., Carbamoyl Phosphate Synthetase 1, A Novel Marker for Gastric Carcinoma, Chinese Medical Journal, 102(8):630-638, 1989, results of immunocytometric investigations on tissue samples from various surgically removed tumors for a possible presence of CPS 1 are reported. The authors found indications of CPS 1 immunoreactivity only in carcinoma tissue from the stomach but not in other tumor tissues (esophagus, large intestine, pancreas, lung, breast, ovary, kidney, prostate and urinary bladder). They derive therefrom a possible suitability of CPS 1 as a selective tissue marker, i.e. cellular tumor marker, for gastric cancer. A possible occurrence of CPS 1 in the circulation is not discussed.

To date, the determination of human CPS 1 in human serum or plasma has been described, in particular in publications of the applicant, only in the case of sepsis patients (cf. WO 03/089933 A1; also see: Joachim Struck et al., Release of the Mitochondrial Enzyme Carbamoyl Phosphate Synthase under Septic Conditions, in: Shock, vol. 23, no. 6, pages 533-538, 2005) and tumor patients (DE 10 2004 039 665.5). Sepsis patients represent a patient population clearly distinguishable from patients who are treated over relatively long periods with drugs owing to different diseases or health abnormalities. The same applies to persons who take potentially harmful addictive substances or stimulants (narcotics, alcohol) over long periods or are exposed to particular risks of other types.

In the case of sepsis patients, a highly acute potentially life-threatening disease is typically monitored and treated in the intensive care ward of a hospital, whereas a conventional drug treatment, for example a treatment with analgesics, antihypertensive agents or psychotropic drugs, frequently only serves for alleviating or eliminating certain pathological symptoms in persons who feel substantially healthy without these symptoms.

In the determination of human CPS 1 in patient sera and plasmas according to the present invention, it is possible in principle to proceed as described in the publication WO 03/089933 A1 of the applicant in relation to the determination of CPS 1 as a sepsis marker. The immunodiagnostic assay method described in the experimental section of the present application is closely related to the method which has already been described in the abovementioned application WO 03/089933 A1 of the applicant.

The method for the determination of CPS 1 in the context of the present application comprises not only the direct immunological determination of CPS 1 in in vitro samples but also the preparatory commercial activities which serve for carrying out the method in the sense of uses of CPS 1 or of antibodies for the selected determination for the production of assay kits, or a use for producing assay components, for example of polyclonal or monoclonal antibodies which, for example in immobilized and/or marked form, are as a rule likewise provided in assay kits for said diseases, or of standard or reference substances if the kits produced are intended for carrying out the method according to the invention or permit it to be carried out.

It should additionally be expressly pointed out that, in the determination according to the invention of CPS 1, depending on assay design, simultaneous determination of CPS 1 both in the form of the substantially complete molecule and in the form of other, shorter fragments (physiologically occurring partial peptides) of the complete CPS 1 which may be present in the biological fluid can occur. Where "determination of CPS 1" is mentioned in the present application, a determination in which in addition to or instead of the complete enzyme CPS 1 the immunologically coreacting fragments thereof are determined or concomitantly determined is also meant. Any improper restrictive interpretation of the teaching of the present invention, and in particular regarding the more specific nature of the analyte CPS 1 determined, is ruled out. A combination measurement in which other liver enzymes are simultaneously determined is also expressly within the scope of the present invention.

In the light of the results of the measurement of a first patient group which are shown below, CPS 1 detectable in plasma or serum is outstandingly suitable for detection, and in particular for early detection before its clinical manifestation, and for monitoring the course and therapy of drug-related liver damage.

For the actual CPS 1 determination, immunoassays of any suitable assay design are preferred.

The immunodiagnostic method for the determination of CPS 1 in a biological sample may be based on any known principles of the immunodiagnostic method which are used for detecting and for measuring antigens. Preferably, CPS 1 is determined with the aid of a ligand binding assay in which specific antibodies suitable for binding and marking are used in immobilized form or marked or markable form.

Competitive assay formats, too, may offer particular advantages. Preferably, instead of working with enzyme marking, another marking is chosen, for example marking for a chemiluminescence detection reaction, e.g. an acridinium ester. Of course, it is preferable to use for the CPS 1 determination an assay which ensures the required high sensitivity in the range of the CPS 1 concentrations occurring and permits separation of the measuring signals from the assay background.

The determination method can be adapted to chip technology or designed as an accelerated test (point-of-care test) which uses, for example, immunochromatographic separation and detection steps.

In a preferred embodiment, the immunodiagnostic determination is carried out as a heterogeneous sandwich immunoassay in which one of the antibodies is immobilized on any solid phase, for example the walls of coated test tubes (e.g. comprising polystyrene; "coated tubes"; CT) or on microtiter plates, for example comprising polystyrene, or on particles, for example magnetic particles, while the other antibody carries a residue which represents a directly detectable label or permits a selective link to a label and serves for the detection of the sandwich structures formed. Delayed or subsequent immobilization with the use of suitable solid phases is also possible.

In principle, it is possible to employ all marking techniques which can be used in assays of the type described, including markings with radioisotopes, enzymes, fluorescent, chemoluminescent or bioluminescent labels and with directly optically detectable color markings, such as, for example, gold atoms and dye particles, as used in particular for so-called point-of-care (POC) or accelerated tests. In the case of heterogeneous sandwich immunoassays, too, the two antibodies may have parts of a detection system of the type described below in relation to homogeneous assays.

The method according to the invention can furthermore be designed as a homogeneous method in which the sandwich complexes formed from the two antibodies and the CPS 1 to be detected remain suspended in the liquid phase. In such a case, it is preferable to mark both antibodies with parts of a detection system which permits signal generation or signal triggering when both antibodies are integrated in a single sandwich. Such techniques can be designed in particular as fluorescence amplification or fluorescence extinction assay methods. A particularly preferred method of this type relates to the use of assay reagents to be used in pairs, as described, for example, in U.S. Pat. No. 4,822,733, EP-B1-180 492 or EP-B1-539 477 and the prior art cited therein. They permit a measurement which selectively detects only reaction products which contain both marking components in a single immune complex, directly in the reaction mixture. As an example, reference is made to a technology available under the brands TRACE® (Time Resolved Amplified Cryptate Emmission) or KRYPTOR®, which implements the teachings of the abovementioned applications.

Instead of an immunodiagnostic determination of CPS 1 or CPS 1 immunoreactivity, it should also be possible for diagnostic purposes to effect the CPS 1 determination optionally also indirectly as a determination of an enzyme activity which corresponds to the CPS 1 activity or the residual activity of the CPS 1 fragments in the blood. Since CPS 1 does not occur in the circulation of healthy persons, a measureable CPS 1 enzyme activity in the blood of a patient may be a diagnostically significant indication of a serious disturbance of the patient's soundness of health.

The content of the prior applications (WO 03/089933 A1; furthermore DE 10 2004 039 665.5) of the applicant is to be regarded as part of the disclosure of the present application by express reference to these applications, in particular regarding the technical feasibility of the CPS 1 measurements in the method according to the invention.

Below, the determination of CPS 1 in plasmas of healthy persons, of patients treated with drugs but without liver damage and of patients treated with the same drugs who suffered drug-related liver damage is explained in more detail, reference being made to a FIGURE and an associated table.

The FIGURE shows the following:

FIG. 1 the results of the measurement of the CPS 1 concentration (in U/ml) in plasmas of healthy normal persons (A) and of patients who were treated with various drugs and who suffered liver damage (C) or who did not suffer liver damage (B), with the use of the immunoassay described in more detail in the experimental section.

EXPERIMENTAL SECTION

The Description of Assay

1. Preparation of the Antibodies a) Immunogens

Two different peptide sequences from the complete sequence of human CPS 1 were chosen, in particular a first peptide sequence 1 (EFEGQPVDFVDPNKQN), which corresponds to the amino acids 184-199 of the sequence of human CPS 1 (cf. peptide PCEN17 according to WO 03/089933), and a second peptide sequence (FHGTSSRIGSSMKS), which corresponds to the amino acids 781-794 of the sequence of human sequence CPS 1. Each peptide was synthesized in a form provided with an aminoterminal cysteine residue (Cys0) by Jerini (Berlin, Germany). The synthesized peptides used for the following immunizations are shown in the sequence listing as SEQ ID NO:1 and SEQ ID NO:2, respectively.

b) Antibodies

For the immunization, the two peptides synthesized were conjugated with hemocyanine from *Limulus Polyphemus*, and, as also described in WO 03/089933, polyclonal antibodies were produced in sheep by Micropharm Ltd. (Carmarthenshire, Great Britain).

2. Purification of the Antibodies

The antibodies were purified by means of ligand-specific affinity purification. For this purpose, the Cys(0) peptides 1 and 2 were first coupled to Sulfo Link gel from Pierce (Boston, USA). The binding was effected according to the manufacturer's instructions.

The procedure was as follows: polycarbonate columns (15 mm×80 mm) were filled with 5 ml of affinity matrix. After equilibration of the columns with PBS (136 mM NaCl, 1.5 mM $KH_2PO_4$, 20.4 mM $Na_2HPO_4.2H_2O$, 2.7 mM KCl, pH 7.2), 5 mg of the respective peptides were weighed, dissolved in PBS and added to the closed columns. The gel material was homogenized by swirling. After incubation for 15 minutes at room temperature and settling of the gel material, the columns were washed with 5×3 ml of PBS. For saturation of free binding sites, in each case 5 ml of a 50 mM L-cysteine solution were added to the column material, and, after homogenization, the gel material was incubated again at room temperature for 15 min. After settling of the gel material, each column was washed six times with 5 ml of a 1M NaCl solution and then washed again with PPS.

The gel material was mixed with 25 ml of the respective antiserum pool and incubated overnight at room temperature with gentle swirling. The serum-gel mixtures were transferred to polycarbonate columns, and excess serum was removed. The columns were then washed with 250 ml of PBS in order to remove unbound serum proteins. The desorption of the bound antibodies was effected by elution of the column with 50 mM citric acid (pH 2.2). The eluate was collected in fractions of 1 ml. The protein concentration of each fraction was determined with the aid of the BCA protein assay kit from Perbio (Bonn, Germany), and the fractions having a protein content >1 mg/ml were combined. The affinity-purified antibodies were buffered by means of dialysis in PBS and, after another determination of the protein content, were then stored at 4° C.

3. Immobilization/Marking of the Antibodies

The purified antibodies against the peptide which corresponds to the amino acid sequence 781-794 were immobilized on polystyrene tubes (Startubes, 12 mm×75 mm, from Greiner, Germany). For this purpose, the antibody solutions were diluted to a protein concentration of 6.7 µg/ml with PBS and 300 µl were pipetted per tube (corresponds to 2 µg of antibody per tube). These were incubated for 20 h at room temperature and then washed three times with 4 ml of PBS each time. The tubes were stored at 4° C. until required for further use.

The antibody (1 mg/ml in PBS) against the peptide which corresponds to the amino acid sequence 184-199 was luminescence-marked with acridinium ester N-hydroxysuccinimide (1 mg/ml in acetonitrile, from InVent, Hennigsdorf, Germany). For the marking, 200 µl of antibody were mixed with 4 µl of acridinium ester and incubated for 20 min, and free acridinium ester bonds were saturated by addition of 40 µl of a 50 mM glycine solution. The marking batch was separated from free acridinium ester by means of HPLC on a BioSil 400 gel filtration column (from BioRad, Munich, Germany). PBS was used as the mobile phase.

4. Relative Calibration

In order to be able to determine the relative CPS 1 concentrations, a pool of plasmas of human patients with SIRS with particularly high CPS 1 concentrations was used as standard material. The CPS 1 concentration of this pool was arbitrarily fixed at 150 U/ml. Starting from this pool, the standards were prepared by serial dilution with CPS 1-free human plasma from healthy persons, to which standards arbitrary concentrations (in relative units, U) were assigned according to their dilution.

5. Assay Procedure

50 µl of a plasma sample and 100 µl of PBS buffer (with 10 mM EDTA) were pipetted per antibody-coated tube and incubated for 16 h at room temperature. After washing three times with 1 ml of PBS each time, 15 ng of the marked antibody (in 200 µl of PBS buffer, 10 mM EDTA) were added per tube. The tubes were incubated for a further 2 h and unbound tracer antibody was then removed by washing five times with 1 ml of PBS each time. Marked antibody bound to the tube was quantified by means of luminescence measurement in a luminometer (Berthold LB 952T/16).

Measurement of EDTA Plasmas of Healthy Persons and of Patients Who are Being/were Treated with Various Drugs 50 plasmas of healthy control patients and 73 plasmas of patients who were treated with various drugs as stated in Table 1, which are known to have potentially liver-damaging activity, were used as test samples for the CPS 1 determinations. The 73 plasmas of patients comprised plasmas of 50 patients for whom no liver damage was found and 23 further plasmas of patients who were treated with the same drugs stated in Table 1 but who had suffered liver damage.

50 µl of standard or sample and 200 µl of assay buffer were pipetted into each of the abovementioned test tubes. Incubation was effected for 18 hours at 20° C. with shaking. Washing was then effected four times with 1 ml of wash solution (0.1% Tween 20) each time per tube. 200 µl of assay buffer, containing 0.5 million RLU of the MA70-marked Tracer antibody, was then pipetted into each tube. Incubation was effected for two hours at 20° C. with shaking. Washing was then effected four times with 1 ml of wash solution (0.1%

Tween 20) each time per tube, the tubes were allowed to drip and the chemiluminescence bound to the tube was measured in a luminometer (from Berthold, LB952T; base reagents Brahms AG).

The concentration of CPS 1 immunoreactivity was read using the software MultiCalc (spline fit). The following results were obtained:

The median of the CPS 1 concentrations measured for the group of 50 healthy persons was 2.4 U/ml.

The results for drug-treated persons without liver damage (B) and drug-treated persons who suffered liver damage (C) are shown in the following table and, alongside the additional measured values for the healthy persons (A), are plotted in the graph in FIG. 1.

TABLE 1

| Medicament | Treated persons without liver damage (B) | Treated persons with liver damage (C) |
|---|---|---|
| Paracetamol | 5 | 2 |
| Statins | 5 | 4 |
| Anabolic steroids | 3 | 1 |
| Halothane | 7 | 2 |
| Chlorpromazine | 5 | 3 |
| Sulfonamides | 4 | 2 |
| Tetracyclines | 6 | 3 |
| Rifampicin | 3 | 3 |
| Captopril | 6 | 2 |
| Ibuprofen | 6 | 1 |

A median of 2.8 U/ml was found for the results of the measurements in the case of 50 patients of group (B) and a median of 253 U/ml for those of group (C).

Concomitant investigations by the applicant have furthermore shown that damage to the mitochondria and associated CPS 1 release from the liver cells occur in the case of liver damage as may typically occur as side effects of drugs, before apoptosis of the liver cells or necrosis of the liver tissue occurs. The CPS 1 release can therefore be found at a time when no other clinical symptoms are as yet observable which, inter alia, subsequently also lead to changes in the concentrations of the traditionally determined liver parameters, e.g. other liver enzymes, which are normally measured at elevated levels only when necrotic processes have begun in the liver.

If the action of the harmful external substance, for example of the drug, is stopped at the stage when substantially only CPS 1 is measured at elevated levels, the damaged mitochondria in the otherwise undamaged liver cells can be replaced and the liver recovers. There is no irreversible liver damage as may occur in the case of a diagnosis which is possible only at a later time and is based on the conventional clinical findings and the known liver parameters, the release of which is associated with necrotic processes.

A prophylactic measurement of CPS 1 in persons who are treated over relatively long periods with drugs, take potentially harmful stimulants and addictive substances or are exposed to an increased risk of developing liver damage owing to their nutritional habits and living conditions can make developing liver damage identifiable at an early time so that counter measures can be initiated at a correspondingly early time (for example the causative drugs can be discontinued) and late damage and the costs associated therewith for the patients and the economy as a whole can be avoided.

If, in addition to CPS 1, the conventional liver enzymes measureable in the serum only at later stages of liver damage are concomitantly determined, conclusions about the stage of liver damage which has already been reached can be drawn from the simultaneous detectability or non-detectability of conventional liver enzymes which indicate necrotization of the liver. Thus, for example, non-detectability of some or all of the concomitantly determined further liver enzymes, such as, for example, GOT (glutamate oxalacetate transaminase), GPT (serum glutamate pyruvate transaminase), GLDH (glutamate dehydrogenase), γ-GT (γ-glutamyl transpeptidase), sorbitol dehydrogenase, alkaline phosphatase, ALT (alanine amino-transferase), AST (aspartate amino-transferase), GDH (glycerol phosphate dehydrogenase), LHD (lactate dehydrogenase), cholinesterase, LAP (leucine amino-peptidase), GGTP (glutamyl transpeptidase) and other liver enzymes determined in the liver diagnosis, means that the liver damage is not yet far advanced and, for example, can be reversed with high probability by termination of exposure, while the simultaneous detectability of some or all of said liver enzymes indicates advanced, possibly already irreversible liver damage. The determination of CPS 1 in a combination measurement is therefore also expressly within the scope of the present invention.

All modern measuring techniques (e.g. chip technology) and evaluation techniques (computer with corresponding evaluation algorithms) available to date for this purpose can be used for such a combination measurement.

Owing to the earlier occurrence of CPS 1 in the blood, carrying out a CPS 1 determination is a possibility also in the testing of new drugs during drug development, in order to identify possible liver-damaging effects of the investigated drug candidates as early as possible and to avoid later harm to the health of patients and financial losses and an adverse effect on image on the part of the manufacturer.

The invention claimed is:

1. An in vitro method for the detection of early-stage reversible liver damage caused by liver-damaging drugs or other substances harmful for the liver, said method comprising:
   (a) determining an amount of human enzyme carbamoyl phosphate synthase (CPS1) or a fragment thereof having CPS 1 immunoreactivity in a serum or plasma sample of a patient who has been exposed to potentially liver-damaging drugs or potentially hepatotoxic substances;
   (b) concomitantly with (a) determining a concentration of at least one of a liver enzyme selected from the group consisting of GOT (glutamate oxalacetate transaminase), GPT (serum glutamate pyruvate transaminase), GLDH (glutamate dehydrogenase), gamma-GT (gamma-glutamyl transpeptidase), sorbitol dehydrogenase, alkaline phosphatase, LT (alanine amino-transferase), AST (aspartate amino-transferase), GDH (glycerol phosphate dehydrogenase), HD (lactate dehydrogenase), cholinesterase, LAP (leucine amino-peptidase), GGPT (glutamyl transpeptidase in said sample;
   (c) comparing the amount of CPS1 or fragment thereof in the sample with an amount of CPS1 in healthy individuals; and
   (d) concluding that early stage liver damage is present in the patient if the amount of CPS 1 in said sample is elevated above the amount of CPS1 in healthy individuals but the concentration in said sample of a liver enzyme determined in (b) is in the normal range.

2. The method of claim 1, wherein the amount of CPS 1 is measured at selectable intervals in patients at risk but without manifest liver symptoms.

3. The Method of claim 1 wherein the determination is carried out by an immunodiagnostic assay.

4. The method of claim 3, wherein the immunodiagnostic assay is a sandwich-type assay selective for human CPS 1.

5. The Method of claim 3, wherein said assay is designed as an accelerated test or POC test (point-of-care test).

6. The Method of claim 1 wherein the determination of CPS 1 is carried out with an assay which identifies intact CPS 1 and/or fragments thereof.

7. The Method of claim 1 wherein CPS 1 is determined in serum or plasma samples of patients who are being treated with drugs which are selected from nonsteroidal antiinflammatory drugs (NSAIDs), analgesics, anabolic steroids, hormonal contraceptives, antigout agents, statins, inhalational anesthetics, antibiotics, sulfonamides, tuberculostatic agents, antitumor agents, psychotropic drugs, cardiovascular agents, phytopharmaceutical drugs, Paracetamol.

* * * * *